United States Patent [19]
Chafetz

[11] Patent Number: 4,532,058
[45] Date of Patent: Jul. 30, 1985

[54] SPIROLACTONE CONDENSATION PRODUCT DISPERSANTS AND LUBRICANTS CONTAINING SAME

[75] Inventor: Harry Chafetz, Poughkeepsie, N.Y.

[73] Assignee: Texaco Inc., White Plains, N.Y.

[21] Appl. No.: 345,861

[22] Filed: Feb. 4, 1982

Related U.S. Application Data

[63] Continuation-in-part of Ser. No. 190,687, Sep. 25, 1980, abandoned.

[51] Int. Cl.³ .............................................. C10M 1/32
[52] U.S. Cl. ................................. 252/51.5 A; 549/265
[58] Field of Search ........................ 252/51.5 A, 56 D; 549/265

[56] References Cited

U.S. PATENT DOCUMENTS

| | | | |
|---|---|---|---|
| 2,301,827 | 11/1942 | Stoll | 260/343 X |
| 3,062,631 | 11/1962 | Thompson | 252/51.5 A X |
| 3,155,686 | 11/1964 | Prill et al. | 260/343.6 |
| 3,734,865 | 5/1973 | Heiba et al. | 260/343.6 X |
| 3,997,569 | 12/1976 | Powell | 260/343.6 X |
| 4,029,675 | 6/1977 | Williams et al. | 260/343.6 X |
| 4,104,477 | 8/1978 | Lavigne | 260/343.21 X |

Primary Examiner—Andrew H. Metz
Attorney, Agent, or Firm—Robert A. Kulason; James F. Young; James J. O'Loughlin

[57] ABSTRACT

Motor oil dispersants are disclosed which are made by heating alkenyl succinic anhydrides in the presence of bases and heating the resulting products with a polyamine $H_2N(RNH)_nH$ or a polyamine alcohol $HO(RNH)_nH$.

Also disclosed are motor oils containing from 0.10 to 10.00 weight percent of at least one such dispersant.

11 Claims, No Drawings

SPIROLACTONE CONDENSATION PRODUCT DISPERSANTS AND LUBRICANTS CONTAINING SAME

BACKGROUND OF THE INVENTION

1. Field of the Invention

This invention relates to novel compositions of matter classified as motor oil dispersants. The invention also is concerned with processes for making sludge dispersants and with motor oils containing them.

Numerous dispersants already have been suggested and tried in motor oils to improve the characteristics thereof. However, continued efforts are constantly being made to find new additives of this type which are economical and are more effective than additives heretofore known in the art. The present dispersants represent the result of one such effort.

2. Description of Prior Disclosures

Little or not prior art of pertinence appears to have surfaced in regard to the present diepersants. Thus Reppe and Mitarbeiter (in Ann. 596,158 (1955) reported the conversion of succinic anhydride to the spirodilactone derived from 4-ketopimelic acid by heating at 190°–200° C. in the presence of sodium benzoate (weak base) catalyst as follows:

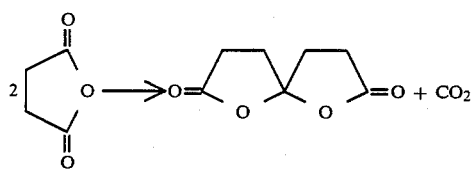

U.S. Pat. No. 4,104,477 is of interest for disclosing spirodilactones formed by intramolecular decarboxylation and cyclization by heating alkenyl or alkyl bis(succinic anhydrides) to a temperature at which one mole of $CO_2$ is lost to give products having a lower molecular weight than the starting anhydrides.

U.S. Pat. Nos. 2,301,827 and 3,155,686 are relevant for showing the preparation of lactones and dilactones. U.S. Pat. Nos. 3,026,631 and 3,734,865 show the reactions of amines with lactones to form different products from those herein.

As will be seen hereinafter, none of these disclose, hint or suggest in any manner applicant's novel and unobvious process and products.

SUMMARY OF THE INVENTION

In accordance with the present invention, there are provided motor oil dispersants prepared by the process which comprises intermolecularly decarboxylating and cyclizing by heating to 180° C. to 270° C. under an inert atmosphere an alkenylsuccinic anhydride (ASAA) having a molecular weight in the range of 1,000 to 22,000 in the presence of about 0.1 to about 10 mole percent thereof of a basic catalyst, to form condensation products and heating these products to 75° to 200° C. with a polyalkylene polyamine of the formula: $H_2N(RNH)_nH$ or a polyalkyleneamino alcohol of the formula $HO(RNH)_nH$ wherein R is a divalent alkenyl group having from 2 to 6 carbon atoms and n ranges from 1 to 6, using a ratio of polyamine or polyamino alcohol to condensation products of about 60:1 to about 0.5:1, followed by separation of the desired product.

Motor oils according to the invention contain from 0.10 to 10.00 weight percent basis oil of at least one of the products prepared by the above process.

DETAILED DISCLOSURE OF THE INVENTION

In respect to the nature of the condensation products formed in the first stage of this invention, infrared spectra showed the weakening or disappearance of the typical ASAA carbonyl absorption bands (1865 and 1790 $cm^{-1}$ C=O stretch bands, and 1070 $cm^{-1}$

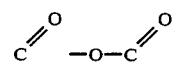

stretch bands) and the appearance of new bands at 1800 and 1770 $cm^{-1}$ (possibly gamma lactones), 1710 $cm^{-1}$ (COOH) and at 1100–1110 $cm^{-1}$

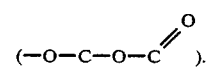

Increases in molecular weight and decreases in saponification number occurred also. Typical products predominantly formed are shown in the following equation:

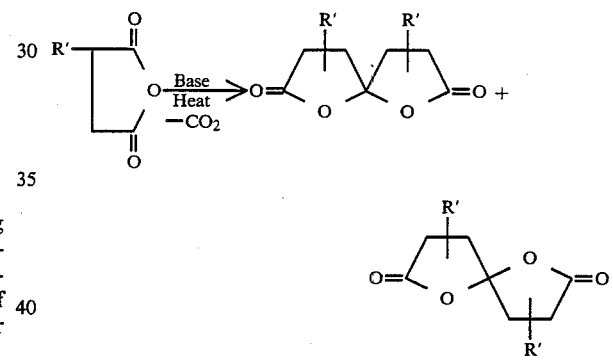

wherein R' is an alkenyl radical having from 64 to 1500 carbon atoms. These products have almost double the molecular weight of the starting anhydrides thus evidencing intermolecular decarboxylation and cyclizing of same. As shown, the spirolactone functionality is in the center as the molecule. It should be noted that other decarboxylation products are possible including olefinic carboxylic acid lactones.

In the preparation of the inventive base-catalyzed ASAA condensation products, the reaction broadly is conducted at 180°–270° C., with 225°–250° C. being preferred. Heating is conducted under an inert atmosphere such as $N_2$ or even $CO_2$ for while $CO_2$ may not be completely inert, it does not interfere with the present reaction.

Suitable catalysts include inorganic bases such as alkali and alkaline earth carbonates, oxides, hydroxides, such as KOH, carboxylates, hydrides, and fluorides. Other basic metal salts and stable organic bases such as amines also are operative. Potassium fluoride and carbonate are preferred.

Catalyst concentration can vary from about 0.1 to about 10 mole % with from about 2 to about 7 mole % being preferred.

The reaction can be conducted at reduced and superatmospheric pressure, but atmospheric pressure is preferable for convenience.

The reaction time ranges from about 0.5 to about 24 hours with the exact time being dependent on the reaction temperature. Usually 2 to 5 hours is sufficient at 225°–250° C.

The alkenylsuccinic anhydrides suitable for this invention broadly are defined by the formula:

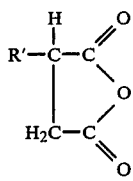

wherein R' is an alkenyl radical having from 64 to 1500 aliphatic carbon atoms.

These alkenyl succinic anhydrides suitably include those of 1,000 to 22,000 average mol weight. The ASAA can be derived from polyolefins such as polyisobutene, polybulytenes and polypropylene. Preferred ASAAs are those having an average molecular weight of 1400 to 3000.

The preparation of the final sludge dispersant additive products is conducted at 75°–200° C., but the preferred range is 110°–160° C. The reaction time is 0.5–10 hr. with the preferred time being 1–2 hours.

The mole ratio polyamine or polyamino alcohol to ASAA-condensation product ranges from about 60/1 to about 0.5/1 with the preferred ratio being from 12/1 to about 2/1 moles of ASAA calculated from Sap. No., assuming two saponifiable groups per molecule.

The polyamines that can be used are defined by the formula above given and include polyethyleneamines, polypropyleneamines, various polyaminopropylamines such as the aminopropylethylenediamines, and hydroxyalkyl substituted polyamines.

The preferred polyamines are those containing from 3–6 amine groups per molecule such as triethylenetetramine and 3-aminopropylethylenediamine.

The invention is further illustrated but not limited by the following examples.

Typical examples of base catalyzed ASAA condensation products are shown in Table I. The reactions were carried out by stirring at atm. pressure under $N_2$ under the conditions shown. The products were used for making dispersants without separation.

Typical examples of the preparation of nitrogenous dispersants by reaction of some of the base-promoted conversion products from ASAA with polyamines (ethylenediamine, EDA; and triethylenetetramine, TETA) are shown in Table II. The reactions were carried out by stirring at atmospheric pressure under $N_2$ using the conditions shown in the tables.

Excess EDA was stripped from the products at about 105° C. at 15–20 mm while excess TETA was removed by extraction with methanol. Some additional preparations of TETA products from treated ASAA are shown in Table III. These preparations used limited amounts of TETA and were not extracted.

The EDA products showed poor dispersancy while the TETA products of the polybutenes of molecular weights 1290 and 2060-treated ASAAs showed fair to excellent dispersancy.

TABLE I

BASE PROMOTED CONVERSIONS OF ASAA'S

| | ASAA[2] | | | Product | |
|---|---|---|---|---|---|
| Ex. | Mol Wt | Sap No. | Reaction Conditions | Sap No. | Mol Wt |
| 1 | 1230 | 62 | 5 hr, 250° C., 0.17 wt % KF | 15 | 1640 |
| 2 | | | 5 hr, 250° C., 0.33 wt % KF | 13 | 1702 |
| 3 | | | 5 hr, 250° C., 0.50 wt % KF | 12 | 1720 |
| 4 | | | 5 hr, 250° C., 0.66 wt % KF | 10 | 1570 |
| 5 | | | 5 hr, 200° C., 0.66 wt % KF | 24 | 1690 |
| 6 | 306 | 362 | 7 hr, 250° C., 0.40 wt % KF | 135 | 656 |
| 7 | | 100 | 5 hr, 230° C., 0.17 wt % KF | 36 | 1120 |
| 8 | | | 5 hr, 230° C., 0.17 wt % KF | 47 | 1040 |
| 9 | | | 5 hr, 230° C., 0.40 wt % $K_2CO_3$ | 34 | 1160 |
| 10 | 1970 | 33 | 5 hr, 250° C., 0.17 wt % KF | 8.5 | 2650 |
| 11 | | | 5 hr, 216° C., 0.17 wt % KF | 16 | 2470 |
| 12 | | | 5 hr, 225° C., 0.40 wt % $K_2CO_3$ | 11 | 2970 |
| 13 | 260 | 368 | 5 hr, 250° C., 0.40 wt % KF | 136 | 455 |

All of the ASAA's are derived from polyisobutylene and contain some unconverted polyisobutylene.

The products of examples 14–30 of Table II were blended into automotive oil compositions and tested by the Bench VC Test which measures the turbidity of a degraded oil, the lower the turbidity values determined the better dispersancy of the oil. This test is carried out by mixing together exact volumes of the test oil, a synthetic blowby, and a mineral oil diluent in a test bottle. The bottle is then placed on a rocker in an oven and rocked for four hours at 280° F. After the heating period ends the sample is diluted with more mineral oil, cooled to room temperature and the sample's turbidity is measured with a Lumetron turbidimeter equipped with a 700 millimicron filter. Synthetic blowby is a hydrocarbon fraction which has been oxidized under specific conditions. This material emulates the oxidized compounds which find their way past the piston rings and into the crankcase of an internal combustion engine. The data are presented in Table III.

TABLE II

BVCT DISPERSANCY RESULTS ON PRODUCTS FROM KF TREATED ASAAs AND POLYAMINES[1]

Ethylenediamine Products (all stripped only)

| Ex. | From KF Treated | Mole Ratio EDA/ASAA Product | Temp % C. | Time Hr | % Diluent Oil | % N | BVCT Results 3% Neat | 4% Neat | Reference Oils Data |
|---|---|---|---|---|---|---|---|---|---|
| 14 | Polybutene (MW 1290) ASAA from Ex 1 | 15/1 | 95 120 | 3 1 | 0 | 0.53 | — | 57.5 | (2.5/16.5/67) |
| 15 | Polybutene (MW 700) ASAA from Ex 7 | 10/1 | 121 | 5 | 0 | 1.1 | $NH^2$ | — | (1.5/25/70) |
| 16 | Polybutene (MW 2060) ASAA from Ex 10 | 58/1 | 16 | 4 | 0 | 0.29 | 47.5 | — | (3.5/23/71.5) |
| 17 | Non KF treated ASAA | 3.7/1 | 95 | 3 | 0 | 1.7 | — | 2.5 | |

TABLE II-continued

BVCT DISPERSANCY RESULTS ON PRODUCTS FROM KF TREATED ASAAs AND POLYAMINES[1]

Polybutene (MW 1290)  120  1

TRIETHYLENETETRAMINE PRODUCTS (ALL EXTRACTED WITH MeOH EXCEPT LAST PRODUCT)

| Ex. | From KF Treated | Mole Ratio EDA/ASAA Product | Temp %°C. | Time Hr | % Diluent Oil | % N | BVCT Results 2% Neat or 4% Dil | 3% Neat or 6% Dil | Reference Oils Data |
|---|---|---|---|---|---|---|---|---|---|
| 18 | Polybutene (MW 1290) ASAA from Ex 1 | 6.8/1 | 160 | 5 | 0 | 0.95 | 41 | 13.5 | (2/18/60.5) |
| 19 | Polybutene (MW 700) ASAA from Ex 7 | 4.2/1 | 160 | 5 | 0 | 1.7 | NH[2] | 31.5 | (1.5/25/70) |
| 20 | Polybutene (MW 2060) from Ex 10 | 12/1 | 160 | 5 | 0 | 0.54 | 19.5 | 7 | (3.5/23/71.5) |
| | *Reference Runs* | | | | | | | | |
| 21 | Non KF treated ASAA polybutene (MW 2060) | 3.1/1 | 160 | 5 | 0 | 1.1 | 3.5 | 3 | (3.5/24.5/74) |
| 22 | Non KF treated ASAA Polybutene (MW 1290) | 0.91/1 | 160 | 2 | 50 | 1.0 | 40.5 33 | 9 8 | (2/15/60.5) (3.5/23/71.5) |

[1]All products made using excess polyamine.
[2]NH means the BVCT conditions yielded a non-homogenous mixture which denoted very poor dispersancy.

TABLE III

BVCT DISPERSANCY RESULTS ON PRODUCTS MADE USING LOWER RATIOS OF TETA TO KF TREATED POLYBUTENE (MW 2060)

| Ex. | Mole Ratio TETA/ASAA Product | Temp °C. | Time Hr | % N | % Diluent Oil | BVCT 2% Neat or 4% Dil | 3% Neat or 6% Dil | Reference Oils |
|---|---|---|---|---|---|---|---|---|
| *KF Treated Polybutene (MW 2060)-ASAA Products* | | | | | | | | |
| 23 | 1.5/1 | 160 | 2 | — | 50 | NH | NH | (3.5/24.5/74) |
| 24 | 1.5/1 | 160 | 5 | 0.49 | 0 | 48 | 37.5 | (3.5/23/71.5) |
| 25 | 1.8/1 | 160 | 2 | — | 50 | NH | NH | (3.5/24.5/74) |
| 26 | 2.4/1 | 160 | 2 | — | 50 | NH | 29.5 | (3.5/24.5/74) |
| 27 | 3.0/1 | 160 | 2 | — | 50 | NH | 205 | " |
| 28 | 3.6/1 | 160 | 2 | — | 50 | NH | 27 | " |
| 29[a] | 2.4/1 | 160 | 2 | — | 50 | 25 | 5.5 | (2.5/18/61) |
| *KF Treated H-300 ASAA Product* | | | | | | | | |
| 30 | 0.89/1 | 140 160 | 2 2 | — | 50 | NH | 29 | (2.5/18/61) |
| *Reference Runs* | | | | | | | | |
| 31[b] | 0.84/1 | 160 | 2 | — | 50 | 24.5 | 9.5 | (3.5/24.3/74) |
| 22[c] | 0.91/1 | 160 | 2 | 1.0 | 50 | 33 | 8 | (3.5/23/71.3) |

[a]K₂CO₃ treated ASAA from Ex. 12 used for this run.
[b]Regular polybutene (MW 2060) ASAA (non-KF treated) used for this run.
[c]Regular polybutene (MW 1290) ASAA (non-KF treated) used for this run.

In motor oils, dispersant molecules are thought to be in equilibrium with micellar molecular aggregates. These micellar aggregates can hold varnish and sludge-forming compounds in colloidal suspension and thereby prevent them from forming harmful deposits. Internal combustion engines normally form varnish- and sludge-forming compounds that contaminate the oil.

Micellar aggregates are shown in the following diagram. It is seen that the aggregates from the claimed products are significantly different from those of typical dispersants such as those described by U.S. Pat. No. 3,734,865, above-mentioned.

Typical Dispersant Micellar Aggregate

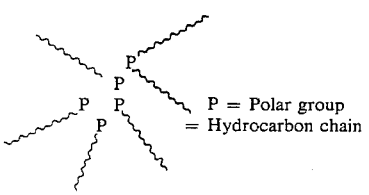

P = Polar group
⁓ = Hydrocarbon chain

Micellar Aggregate From Dispersants Of This Invention

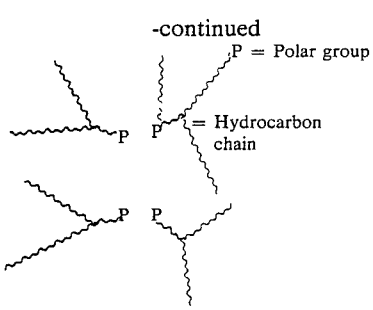

Another advantage of the instant dispersants is their higher molecular weight. That is, since the molecular weight of the spirodilactones is almost twice that of the starting alkenylsuccinic anhydrides, it becomes easy to make higher molecular weight dispersant intermediates from lower molecular weight starting materials. It is widely accepted that higher molecular weight improves dispersancy.

The motor oil compositions of the invention can also contain a combination of other well known additives in an amount sufficient to achieve each additive's function. Lubricating compositions according to this invention comprise a major amount of any of the well known types of oils of lubricating viscosity suitable base oil. They include hydrocarbon or mineral lubricating oils of naphthenic paraffinic and mixed naphthenic and paraffinic types. They may be refined by any of the conventional methods such as solvent refining and acid refining. Synthetic hydrocarbon oils of the alkylene polymer type or those derived from coal and shale may also be employed. Alkylene oxide polymers and their ethers and esters in which the terminal hydroxyl groups have been modified are also suitable. Synthetic oils of the dicarboxylic acid ester type including dibutyl adipate, di-2-ethylhexyl sebacate, di-n-hexyl dodecanedioate, dilauryl azelate, and the like may be used. Alkylbenzene types of synthetic oils such as tetradecylbenzene, etc., are also included.

It is to be understood that the examples presented herein are intended to be merely illustrative of the invention and not as limiting it in any manner; nor is the invention to be limited by any theory regarding its operability. The scope of the invention, therefor, is delineated solely by the appended claims.

What is claimed is:

1. Dispersant additives for motor oils comprising products prepared by the process which comprises, intermolecularly decarboxylating and cyclizing by heating to about 180° C. to about 270° C., under a substantially inert atmosphere, an alkenylsuccinic anhydride of the formula:

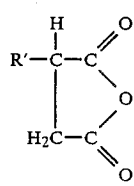

wherein R' is an alkenyl radical having from about 64 to 1500 aliphatic carbon atoms and having a molecular weight in the range of about 1000 to about 22,000
in the presence of about 0.1 to 10 mole percent thereof of a basic catalyst to form bicyclic spirodilactone condensation products represented by the formula:

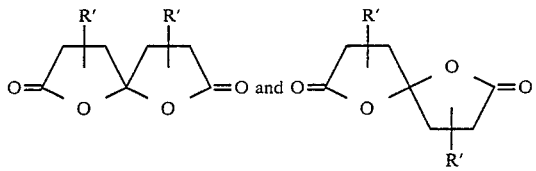

wherein R' is as above; and the spirolactone function is substantially in the center of the molecules and,
heating said products to about 75° to 200° C. with a polyamine or polyamine alcohol of the formulas:

$$H_2N(RNH)_nH \text{ and } HO(RNH)_nH$$

wherein R is a divalent alkenyl group having from about 2 to 6 carbon atoms and n ranges from 1 to 6, using a ratio of said polyamino or polyamine or polyamino alcohol to said condensation products of about 60:1 to about 0.5:1.

2. Additives according to claim 1, wherein said catalyst consists of potassium fluoride or potassium carbonate.

3. Additives according to claim 1 wherein said heating is effected under a nitrogen or carbon dioxide atmosphere.

4. Additives according to claim 1 wherein said anhydride has an average molecular weight of about 1,400 to about 3,000.

5. Additives according to claim 1 wherein there is used a ratio of polyamine or polyamino alcohol to condensation products ranging from about 12:1 to about 2:1.

6. Additives according to claim 1 wherein there is used from about 2 to 7 mole percent of catalyst.

7. Additives according to claim 1 wherein said amine is triethylene tetramine.

8. A motor oil containing a major amount of an oil of lubricating viscosity and a minor, effective sludge dispersant, amount of at least one additive as defined by claims 1, or 2.

9. The motor oil of claim 8, containing from 0.10 to 10.00 weight percent, basis oil, of said additive.

10. A process for preparing a sludge dispersant for motor oils comprising the steps of:
intermolecularly decarboxylating and cyclizing by heating to about 180° C. to about 270° C. under a substantially inert atmosphere an alkenylsuccinic anhydride of the formula:

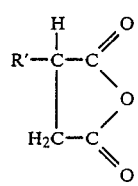

wherein R' is an alkenyl radical having from about 64 to 1500 aliphatic carbon atoms and having a molecular weight in the range of about 1000 to about 22,000;
in the presence of about 0.1 to 10 mole percent thereof of a basic catalyst;

to form bicyclic spirodilactone condensation products represented by the formula:

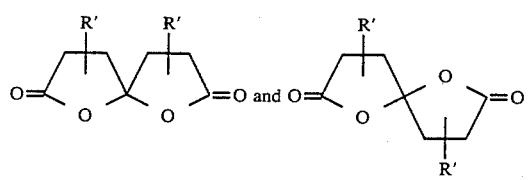

wherein R' is as above; and the spirolactone function is substantially in the center of the molecules; and, heating said products is about 75° to 200° C. with a polyamine or polyamine alcohol of the formulas:

H$_2$N(RNH)$_n$H and HO(RNH)$_n$H wherein R is a divalent alkenyl group having from about 2 to 6 carbon atoms and n ranges from 1 to 6, using a ratio of said polyamino or polyamine or polyamino alcohol to said condensation products of about 60:1 to about 0.5:1.

11. The process of claim 10, wherein there are used a ratio of polyamine or polyamino alcohol to said condensation products of about 12:1 to about 2:1 and from about 2 to about 7 mole percents of said catalyst.

* * * * *